United States Patent [19]

Wadman et al.

[11] Patent Number: 5,380,297
[45] Date of Patent: Jan. 10, 1995

[54] SYRINGE

[75] Inventors: Alexis A. F. Wadman, Bedfordview; Hendrikus J. V. D. Meyden, Edenvale, both of South Africa

[73] Assignee: Inject Development Limited, Tortola, Virgin Islands (Br.)

[21] Appl. No.: 98,451

[22] Filed: Jul. 27, 1993

[30] Foreign Application Priority Data

Jul. 28, 1992 [ZA] South Africa ............... 92/5651
Oct. 21, 1992 [ZA] South Africa ............... 92/8125

[51] Int. Cl.6 ........................................ A61M 5/32
[52] U.S. Cl. ................................ 604/195; 604/197
[58] Field of Search ............... 604/110, 192–198, 604/231, 263

[56] References Cited

U.S. PATENT DOCUMENTS

| | | | |
|---|---|---|---|
| 3,841,329 | 10/1974 | Killinger | 604/231 |
| 3,906,947 | 9/1975 | Cloyd | 604/231 |
| 4,175,704 | 11/1979 | Cohen | 604/198 |
| 4,741,737 | 5/1988 | Meyer et al. | 604/231 |
| 4,826,489 | 5/1989 | Haber et al. | |
| 4,898,589 | 2/1990 | Dolgin et al. | 604/198 |
| 4,908,022 | 3/1990 | Haber | |
| 4,915,699 | 4/1990 | Kornberg | |
| 4,927,414 | 5/1990 | Kulli | |
| 4,936,830 | 6/1990 | Verlier | 604/195 |
| 5,019,044 | 5/1991 | Tsao | |
| 5,085,640 | 2/1992 | Gibbs | |
| 5,098,390 | 3/1992 | Wallingford | 604/195 |
| 5,104,378 | 4/1992 | Haber et al. | |
| 5,106,379 | 4/1992 | Leap | |
| 5,112,316 | 5/1992 | Venturini | 604/195 |
| 5,120,310 | 6/1992 | Shaw | |
| 5,171,300 | 12/1992 | Blake, III et al. | 604/110 |
| 5,215,533 | 6/1993 | Robb | 604/198 |

FOREIGN PATENT DOCUMENTS

| | | | |
|---|---|---|---|
| 8833091 | 6/1992 | Australia | |
| 0334207 | 12/1903 | France | 604/231 |
| 2653667 | 2/1989 | France | |
| 2650187 | 3/1990 | France | |
| 0388200 | 1/1924 | Germany | 604/192 |
| 9105578 | of 0000 | WIPO | |
| 8905795 | 12/1989 | WIPO | |
| 9100144 | 2/1991 | WIPO | |
| 9100005 | 4/1991 | WIPO | |

Primary Examiner—C. Fred Rosenbaum
Assistant Examiner—Frank Wilkens, III
Attorney, Agent, or Firm—Jones, Day, Reavis & Pogue

[57] ABSTRACT

A syringe comprises a barrel with a reciprocable piston having a liquid passage between the piston ends. The outer piston end is connectable to a needle, and an open ended tubular sheath having a needle and a handle end, and being slidable over the barrel, and attachable to the piston, to extend around the barrel when the piston is toward the handle end of the barrel. The piston is selectively detachable from the sheath, and is movable, after such detachment and with retraction of the barrel from the sheath, to selectively draw a needle means attached to the piston into the sheath.

21 Claims, 14 Drawing Sheets

SYRINGE

THIS INVENTION relates to a syringe, and more particularly to the type of syringe known as a "safety" syringe.

BACKGROUND TO THE INVENTION

With the increasing awareness of the possibility of infection from the needle of a used syringe, numerous devices are being proposed for the protection of persons from contact with used syringe needles.

Amongst these devices are syringe disposal units which enable the needles to be disposed of in a receptacle without hand contact with the needle, and needle incinerators which destroy the needle.

Also proposed are a variety of protective devices which guard the used needle against accidental contact.

One class of such devices includes a sheath which is locatable over the needle. Examples of such art are U.S. Pat. No. 5,106,379, which provides a sheath around a syringe barrel, which sheath is triggerable to move forward under spring biasing and extend around the needle in a locked position. Another such sheath device is provided in Patent Cooperation Treaty Application WO 90/07349, which allows for the needle to be retractable within a surrounding sheath, but is concerned particularly with protection from a needle during repeated use, typically during aspiration for blood for intra-muscular injection, or finding a vein for intravenous injection. A further example of a sheath device is in French Patent 90 02944. The latter sheath devices provide for the retraction of the needle into the sheath, at the end of a sheath movement. A variety of mechanisms for attaching the needle to the end of the sheath are provided.

A further example of an outer sheath is provided in U.S. Pat. No. 4,915,699, which allows for an outer sheath around a considerably shorter barrel, which can slide rearwardly within the sheath on final retraction of the sheath within the barrel. Variable friction provides for the injection sliding action between barrel and sheath, to take preference to the movement of the barrel within the outer sheath.

Another variation on this theme is for the needle assembly to be urged into a hollow sheath to surround the needle. An example of this art is U.S. Pat. No. 4,927,414, which allows for the needle to be retracted into a hollow sheath.

The mechanism for achieving this is exceptionally complicated and would be expensive to manufacture. Patent Cooperation Treaty Application WO 91/10461 also provides for such a device, there being an actuator at the end of the sheath which causes the needle and its mounting to detach and move into a chamber within a hollow sheath.

The general art is characterised by complexity of mechanisms, and a multiplicity of parts. This requires numerous moulds, and a multiple step assembly process which all leads to additional costs. It is considered that one of the largest applications for the use of disposable safety syringes is in the disadvantaged communities of the world, and that the cost of such syringes in these environments is critical. Unless a disposable safety syringe can be produced at a cost which is only a small premium over the cost of an ordinary disposable syringe, it cannot be commercially viable.

OBJECT OF THE INVENTION

It is an object of this invention to provide a syringe which can alleviate the abovementioned difficulties.

SUMMARY OF THE INVENTION

In accordance with this invention there is provided a syringe comprising: a barrel having a needle and a handle end; a piston having an operatively inner and outer end, and which is reciprocable in the barrel with the outer end facing the needle end of the barrel, there being a liquid passage between the piston ends, which passage is connectable at the outer piston end to needle means; an open ended generally tubular sheath having a needle and a handle end, and being slidable over the barrel, the sheath further being attachable to the piston to extend around the barrel when the piston is toward the handle end of the barrel; the piston being selectively detachable from the sheath and being movable, after such detachment and with retraction of the barrel from the sheath, to selectively draw a needle means attached to the piston in use, into the sheath.

A feature of the invention provides for the handle end of the sheath to extend over the barrel to the general location of the piston when the piston is attached to the sheath in use, and for the handle end of the sheath to carry finger supports.

Preferably the piston is elongate, having a piston head at its inner end which is sealingly reciprocable with the barrel and which has attachment means at its outer end for enabling the piston to be attachable to the sheath, and the attachment means includes clip means with release means, operable from the interior of the sheath to unclip the piston assembly from the sheath.

Further preferably the barrel has a needle end shaped to operate the release means in use, when the barrel is pushed fully into the sheath, and the clip means are radially outwardly biased clips which are clippable over generally radially inwardly directed surfaces of the periphery of the needle end of the sheath.

There is provided for the clips to have surfaces which slope radially outwardly towards the inner piston end in use, to grip the sheath surfaces in barbed manner against axial retraction in a direction away from the needle end, the clip means having tensioning members positioned to bear in use against an inside surface of the sheath end, to draw the engaged clips tightly against the sheath end.

The release means has at least one lever which is generally axially movable to pivot the clips radially inwardly out of engagement with the sheath end. The needle end of the barrel is shaped to be engageable with the release means by abutting a lever of the release means with axial movement of the barrel, to move the lever axially towards the needle end to pivot the clips out of engagement.

There is also provided for the needle end of the barrel to be locatable around the ends of the levers when the levers are in a radially inwardly and resiliently compressed position, on first insertion of the barrel into the sheath, the levers being biased to move radially outwardly into the path of axial movement of the barrel, after withdrawal of the barrel end from its location around the lever ends.

The piston is preferably a piston assembly which has a piston head sealingly reciprocable within the barrel, and which has an elongate tapering tubular wedge extending co-axially from the piston head towards the operative needle end of the syringe, and which wedge is located within an outer tubular sheath carrying the clipping means, with the wedge having an axial slot running the full length thereof which, together with the outer sheath, provides the liquid opening through the piston itself.

Alternatively the piston is a piston assembly which has a piston sealingly reciprocable within the barrel and which has a tube with a tapering tube opening extending from a widest part at the piston head, and carrying the clipping means towards the other end thereof, the barrel carrying a drive rod slidable within, and which tapers to conform with, the interior taper of the tube, so that with the piston head up against the interior of the handle end of the barrel, the drive rod is snugly fitted within the interior of the tapered portion of the tube of the piston assembly.

Further alternatively, the sheath is a double walled tube joined at the needle end, and the piston is attachable to the end of the interior tube, which tube is reciprocably movable with the piston within the barrel, the barrel being received between the interior and exterior sheath walls during such movement.

The piston may be detachable from the sheath by the breaking of a joint between the interior and exterior tubes of the sheath, along a line of weakening.

The line of weakening is preferably located on the support tube at a position removed from the needle end of the sheath, and selected so that an inwardly extending tubular skirt remains after the said breaking along the lines of weakening in use.

There is provided for there to be formations which hold the sheath in position when the piston is retracted with the barrel, and preferably the formations hold the sheath so that reversal of the action is at least inhibited.

An off-centre resilient bias can be provided in the piston for causing the piston assembly to tilt off centre when the piston is retracted together with the barrel in use, the tilt being arranged to direct an operatively attached needle means towards the sheath wall behind the said remaining skirt.

The piston may alternatively be attachable to, and detachable from, the sheath by means of a rotatable lock.

The piston is shaped to fit within the barrel sufficiently tightly to cause the piston to move with the barrel in use when the piston is detached from the sheath.

The invention extends to a piston, a sheath, and a barrel adapted for use in the syringe defined above. The invention also extends to a hypodermic needle means specifically adapted for use with the syringe defined above.

BRIEF DESCRIPTION OF THE DRAWINGS

Preferred embodiments of the invention are described below by way of example only, and with reference to the accompany drawings, in which.

DETAILED DESCRIPTION OF THE DRAWING

Referring to FIGS. 1 to 6, a syringe (1) has a barrel (2) which is tubular and has a needle end (3) which is open, and a closed handle end (4) with an annular radially extending flange (5) forming a finger grip.

Figure 1:
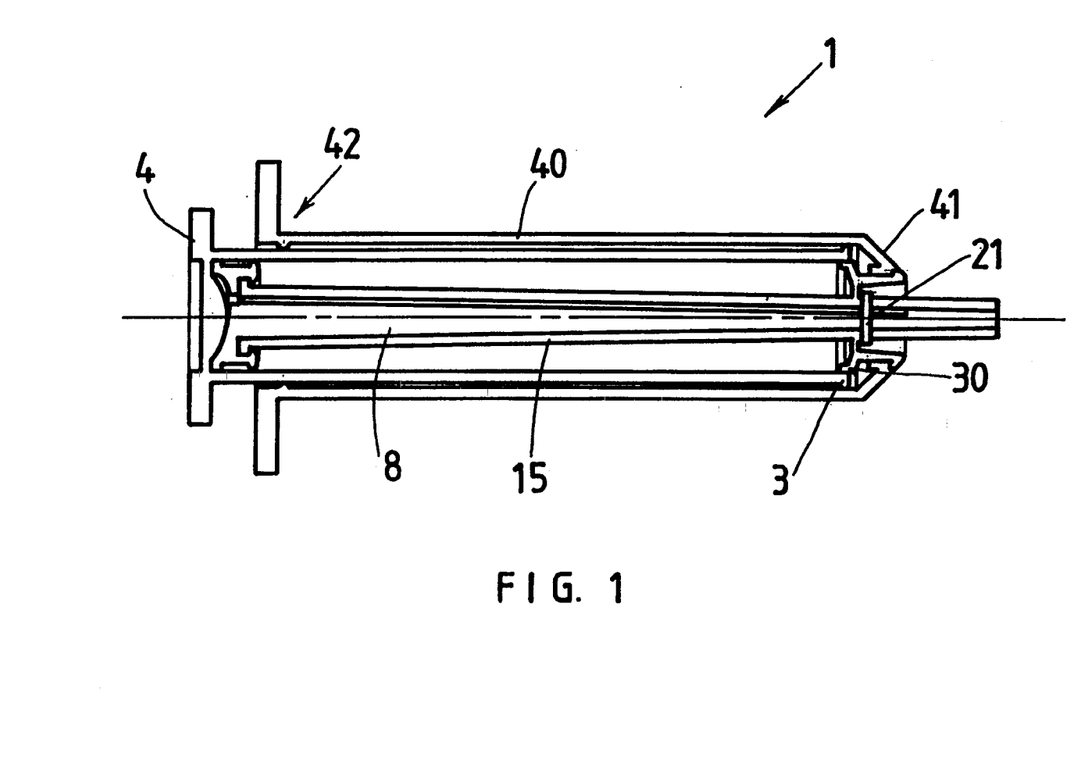
FIGS. 1 to 5 are longitudinal cross sectional views of a first embodiment of the invention in stages of use from assembly through to first charging, discharging, and withdrawal of the needle to a safe position.
Figure 6:
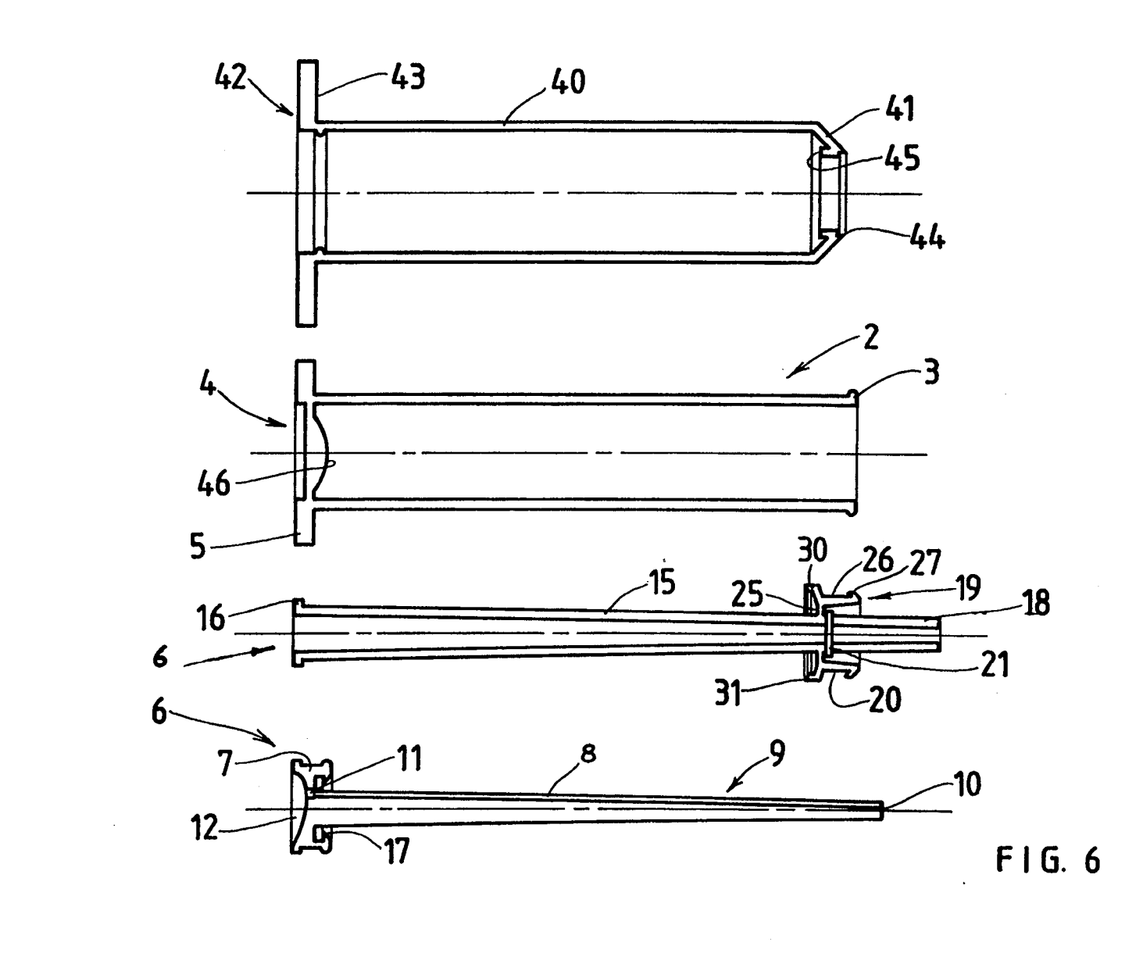
FIG. 6 is a disassembled view of the elements of the embodiment of FIGS. 1 to 5.

An elongate two part piston (6) is reciprocable within the barrel in a sealing manner, and comprises a piston head portion (7) carrying the seal which divides the interior of the barrel from the remainder of the syringe. The head has a co-axially extending tapering rod (8) extending towards the operative needle end of the syringe. The rod has a longitudinal keyway (9) extending its length from the needle end (10) thereof to an opening (11) through the head into a dish shaped recess (12) in the face or inner end of the head.

The second part of the piston is an outer tubular sheath (15), which is locatable co-axially around the rod (8), and has flanges (16) at a head end which locate securely within clipping formations (17) on the outer face of the head. Towards the opposite end of the outer sheath, forming the needle end (18), is located a clipping means (19).

The clipping means has a pair of diametrically opposed radially outwardly extending clips (20), for engaging over the outer end of a sheath, described below. A pair of resilient tensioning tabs (21) are located diametrically opposed to each other on an axis at 90° to the clips (20), and extend radially outwardly to be engageable on the inside surface of the same end of the sheath referred to above.

Each clip (20) has an integral hinge (25) by which it is attached to the sheath (15), and has an axial clip position (26) extending from a base at the hinge, towards the needle end, where it terminates in a barbed hook portion (27) directed back to the piston head end (16) of the sheath. A lever (30) extends generally further radially outwardly in line with the hinge (25) at the base of the clip portion, and has at each end, a lug (31) extending axially rearwardly towards the piston head end (16).

A protective sheath (40) is tubular, having an open needle end (41) at the needle end of the assembled syringe, and an opposite handle end (42) which is open, and which has a radially outwardly extending finger tab (43). The needle end (41) of the sheath has an annular recess (44) in its end face, with a sloping base to receive the barbed hook portions (27) of the clips (19). On the inner side, is an annular bearing surface (45), arranged to be abutted by the tensioning tabs (21).

To assemble the syringe (FIG. 1) the piston head part (8) is inserted within the outer tubular sheath (15) which is engaged with its flanges (16) in the formation (17). In this position the keyway (9) and the opening (11) together form an opening through the assembled piston from the head (7) to the needle end (10).

The assembled piston is then inserted into the barrel (2) with the head fully slid up to and abutting the inside surface of the handle end (4) of the barrel. The barrel is provided with a convex surface (46) on the inside to complement the dish shaped recess (12) in the piston head. In this position, the needle end (3) of the barrel is located around the levers (30), so that the bearing surface of the lug (31) is within the end of the barrel. This further tensions the clips (27) to a radially outward position by pivoting them outwardly about their hinges (25).

The final step in the assembly is the insertion of the syringe barrel with piston assembly as described above, into the protective sheath (40). Insertion takes place through the handle end (42) towards the needle end (41). The assembly is pushed into the sheath (40) until the clips (27) slide over the rebate of the recess (44) in the needle end (41) of the sheath. At the same time, the tensioning tabs (21) bear up against the inside surface (45) of the needle end of the sheath, thus clipping the clip formation under tension between the inside and outside annular surface of the sheath end.

In use, the syringe is fitted with a needle (not shown) on the outer sheath end (18) of the piston, which extends beyond the end of the sheath (40).

Figure 2:
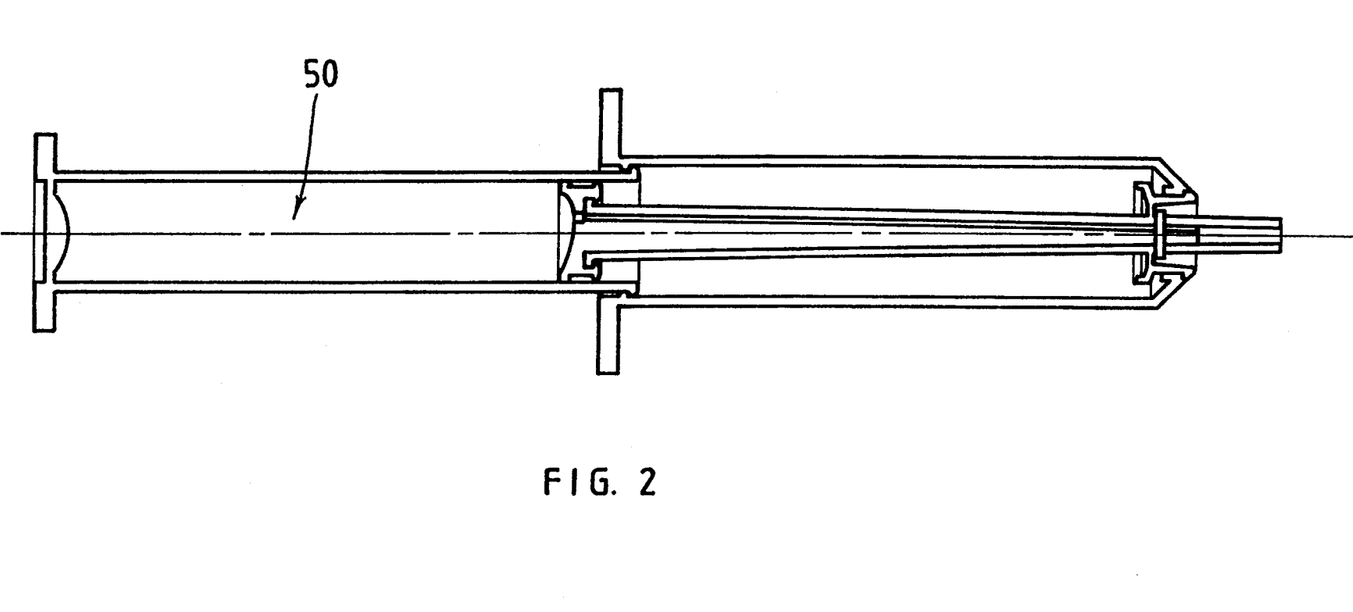

The barrel (4) is then withdrawn to draw in liquid through the needle and the keyway passageway (9), and the piston opening (11), into an interior space (50) formed between the piston head (7) and the interior of the withdrawn barrel.

In this position (as shown in FIG. 2), the end (3) of the barrel has been moved off the lever ends (30) of the clip formations. This causes the lever ends to move under resilient forces outwardly, and into the path of axial movement of the barrel end (3).

Figure 3:
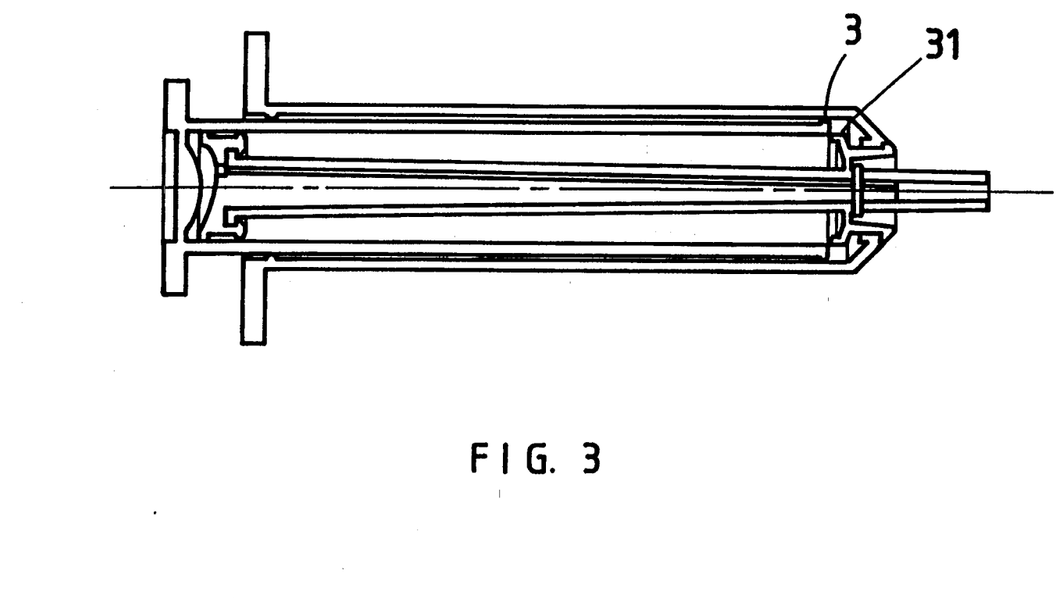
Figure 4:
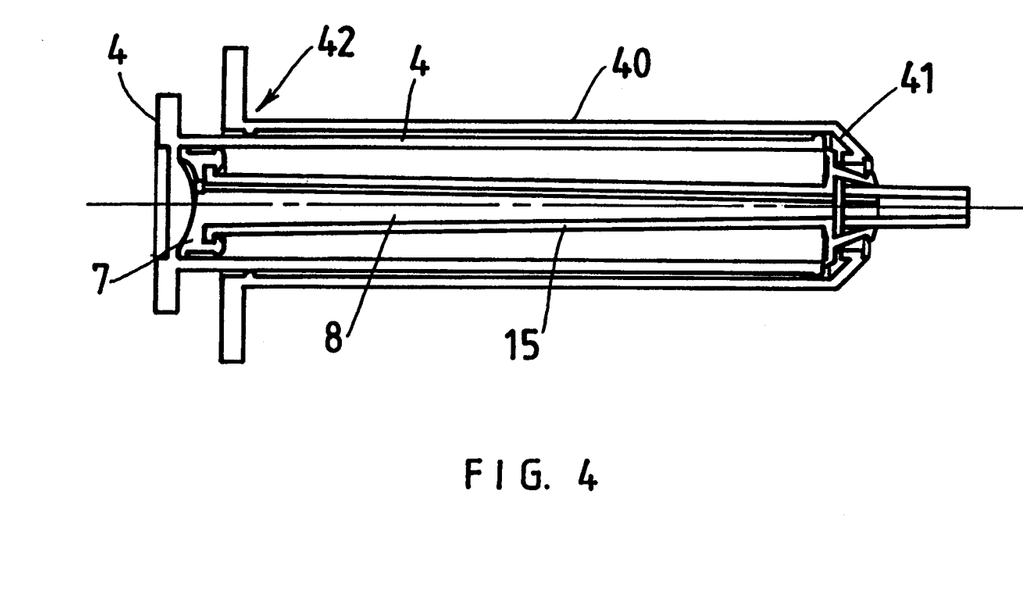

Once an injection site is selected and the needle inserted, the barrel is depressed into the sheath over the piston, causing ejection of the fluid, in normal manner (FIG. 3). At the end of piston travel within the barrel, the ends (3) of the barrel now abut the tabs (31) of the levers of the clipping means, which have moved into the path of axial movement of the end (3). Further depression of the barrel into the sheath (40) causes engagement of the lever means and movement thereof (FIG. 4) to pivot the clipping ends (27) out of engagement with the end of the sheath (40). The clipping formation is now free to move. The friction fit between the piston head is sufficient to cause the piston to move with the barrel under the circumstances, and the barrel can be withdrawn once again from the sheath (FIG. 5) carrying the piston assembly and the needle (not shown) mounted at the end thereof, with it. At the end of withdrawal, the needle is securely housed within the sheath (40).

Figure 5:
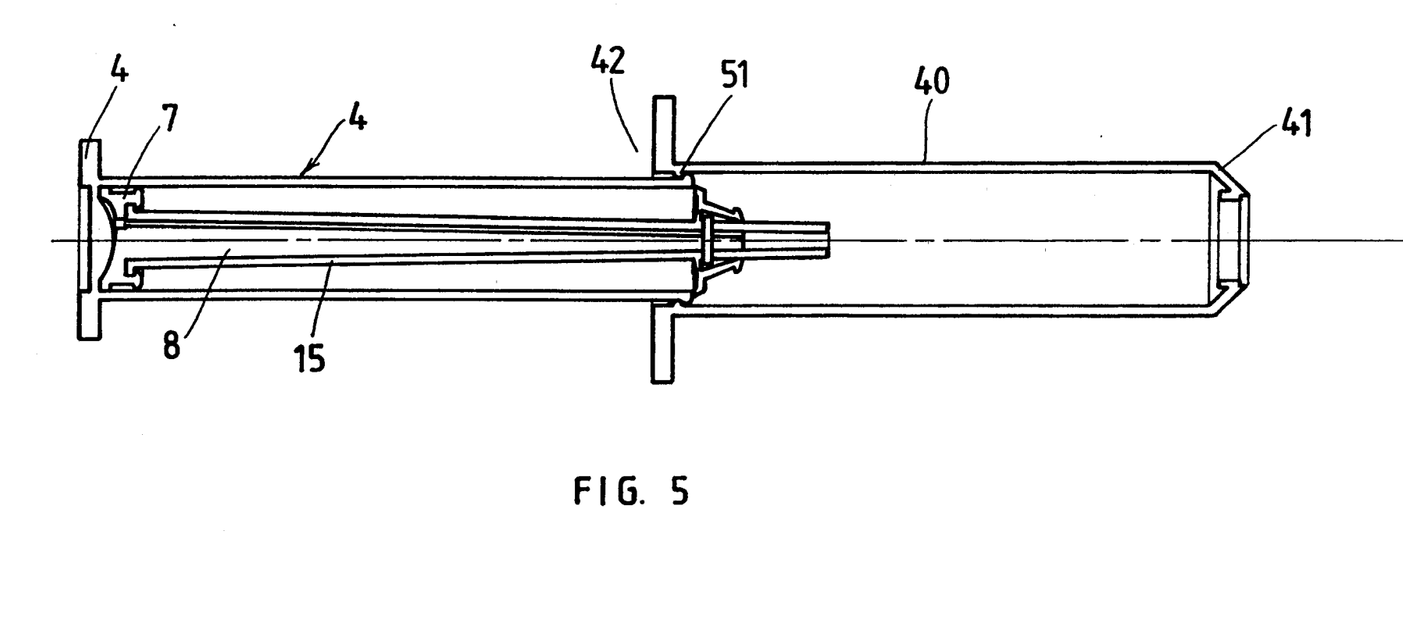

Clipping formations (51) are preferably provided in the handle end of the sheath and the needle end of the barrel, to secure the parts relative to each other in the safety position where the needle is withdrawn within the sheath.

Figure 7:
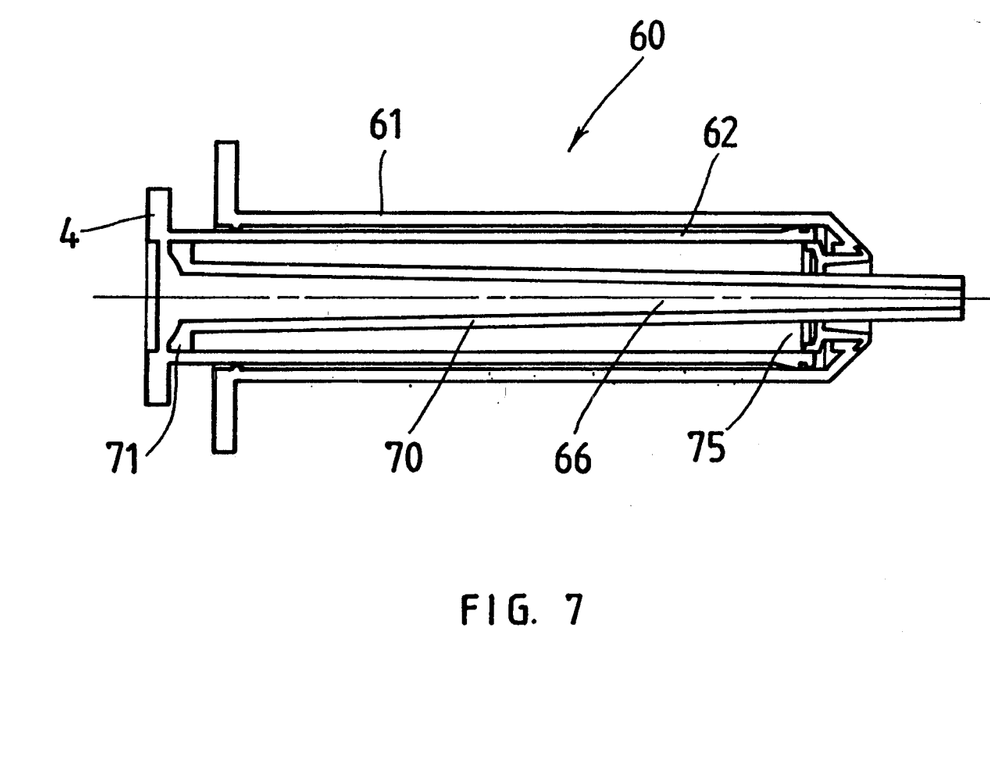
FIGS. 7 to 11 are longitudinal cross sectional views of a second embodiment of the invention in stages of use from assembly through to first charging, discharging, and withdrawal of the needle to a safe position; and, FIG. 12 is a disassembled view of the components of the embodiment of FIGS. 7 to 12.
Figure 12:
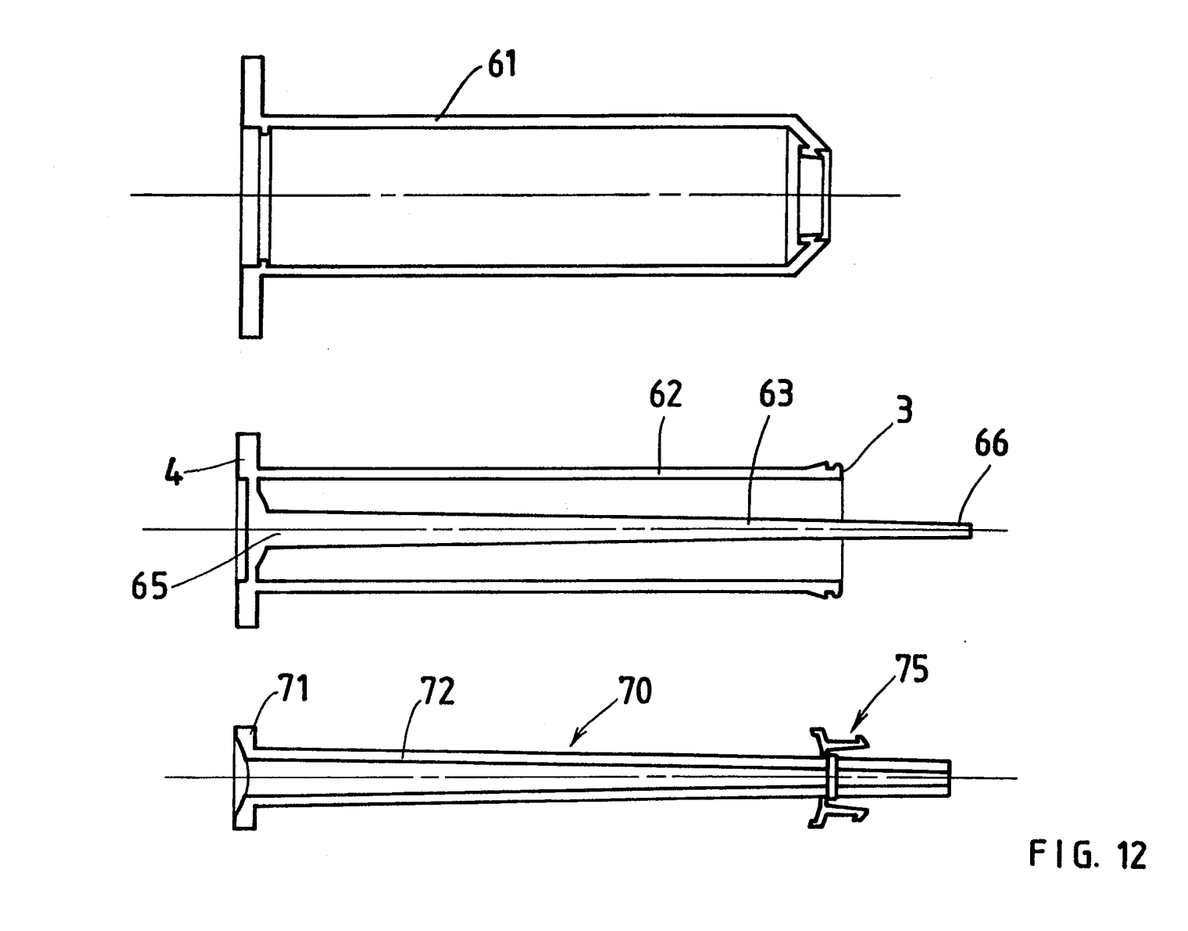

Referring to FIG. 7 and FIG. 12, a second embodiment of the syringe is shown. Many similarities exist between the two embodiments, and like numerals in FIGS. 7 to 12 indicate like elements as described with reference to FIGS. 1 to 6.

A syringe (60) has a protective sheath (61) substantially as described with reference to the previous embodiment, and a syringe barrel (62) which is also substantially as described previously, but which has a drive rod (63) extending co-axially within it from the handle end (4) to extend out of the needle end (3).

The rod tapers from a widest portion (65) at its base where it is secured to the interior of the handle end (4), to a narrowest portion (66) where it extends out of the end of the barrel. The piston (70) in this embodiment, is of one piece only, having a piston head (71) which is sealingly reciprocable within the barrel, and having a tube (72) similar to the assembled outer sheath (15) and rod (8) of the previous embodiment. The opening in the tube has a taper matching that of the drive rod (63). The outer sheath (72) carries a clipping formation (75) which is as described previously.

The syringe (60) is assembled (FIG. 7) by inserting the piston (70) inside the barrel, with the drive rod (63) extending within the opening through the tubular sheath (70). The piston head (71) abuts the interior of the handle end (4) of the barrel, and the rod (63) fills the entire interior of the sheath (72). The needle end (3) of the barrel is located around the levers of the clips, as previously described.

The action of the clip in this second embodiment in conjunction with the sheath and the barrel, to secure withdrawal of a needle within the sheath, is exactly as previously described with reference to FIGS. 1 to 6.

Figure 8:
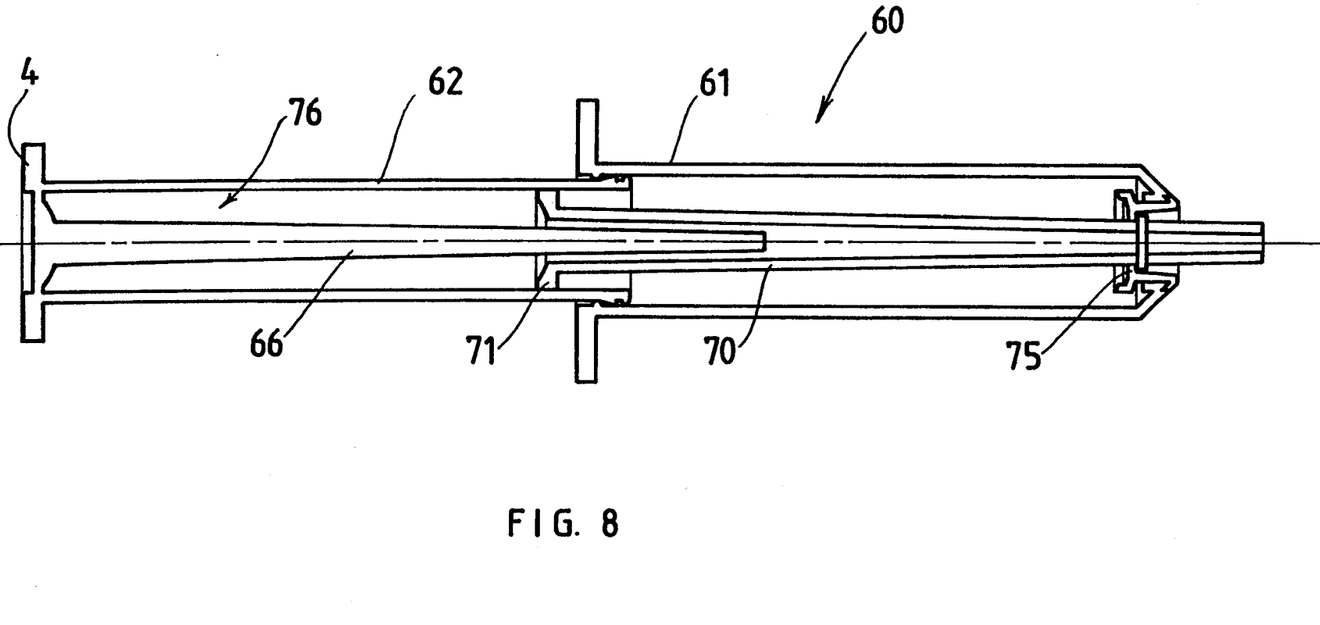

To charge the syringe (60), the barrel is withdrawn from the sheath and the drive rod (63) is withdrawn from the sheath (70) thus opening it up and drawing liquid into the void (76) within the barrel and around the drive rod (63) (FIG. 8).

Figure 9:
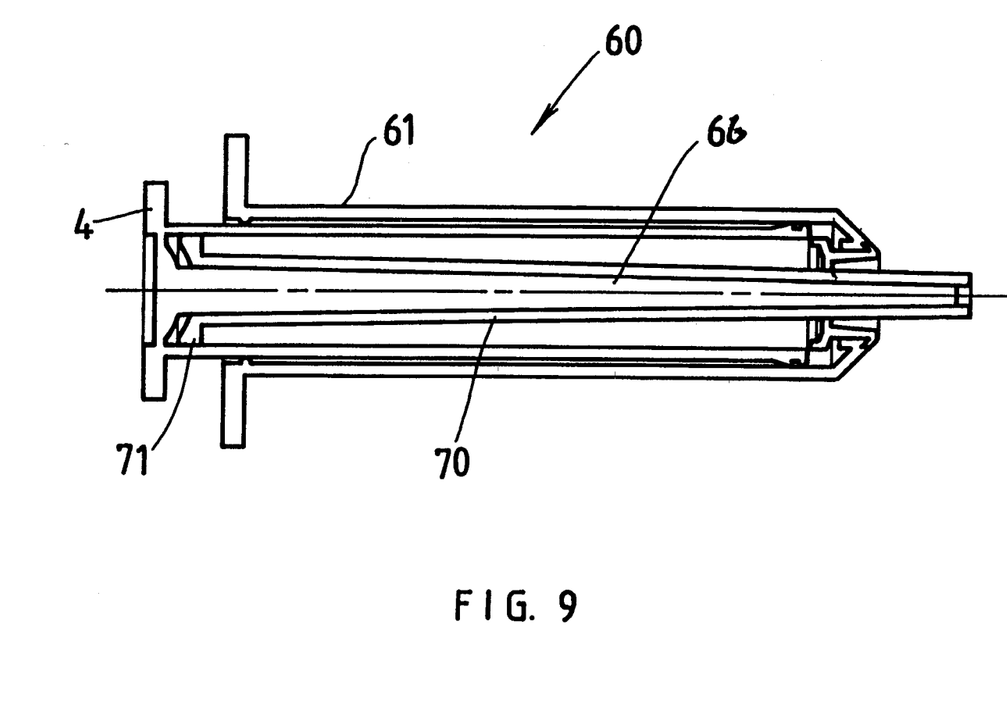

On discharge (FIG. 9) the rod pushes down through the sheath (70), thus ejecting all the liquid therein, and as the piston head comes into contact with the interior of the barrel, the rod seals the end thus ensuring that no liquid is wasted. At this time, the free end (3) of the barrel is abutting the edges of the clip formation, as described with reference to FIG. 3.

Figure 10:
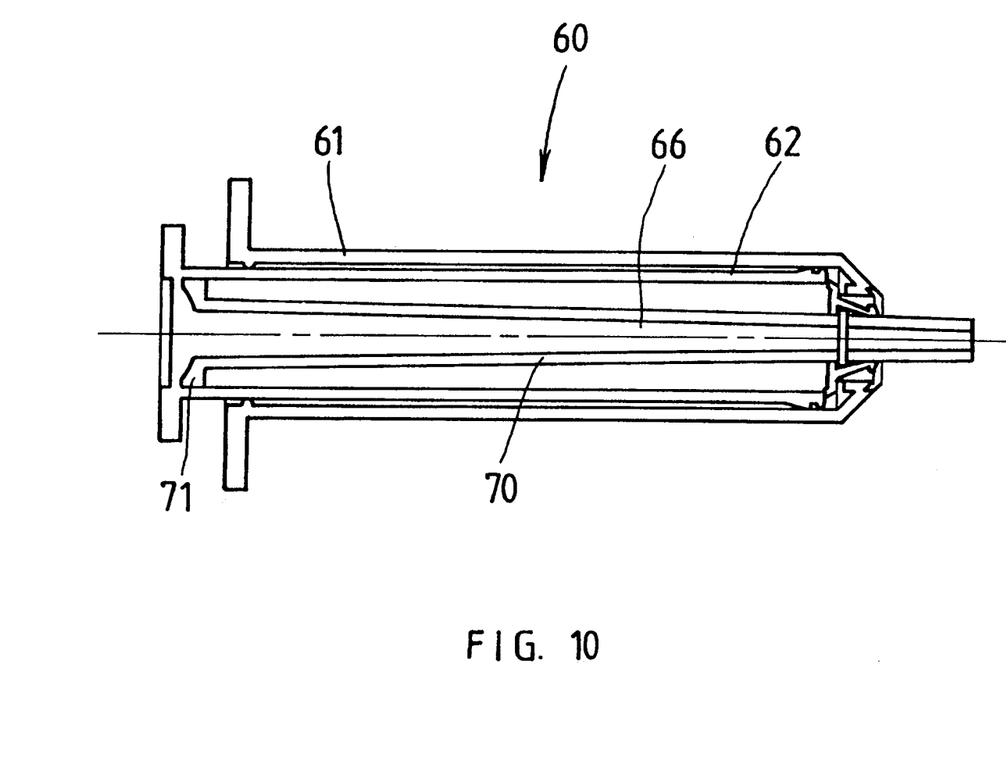
Figure 11:
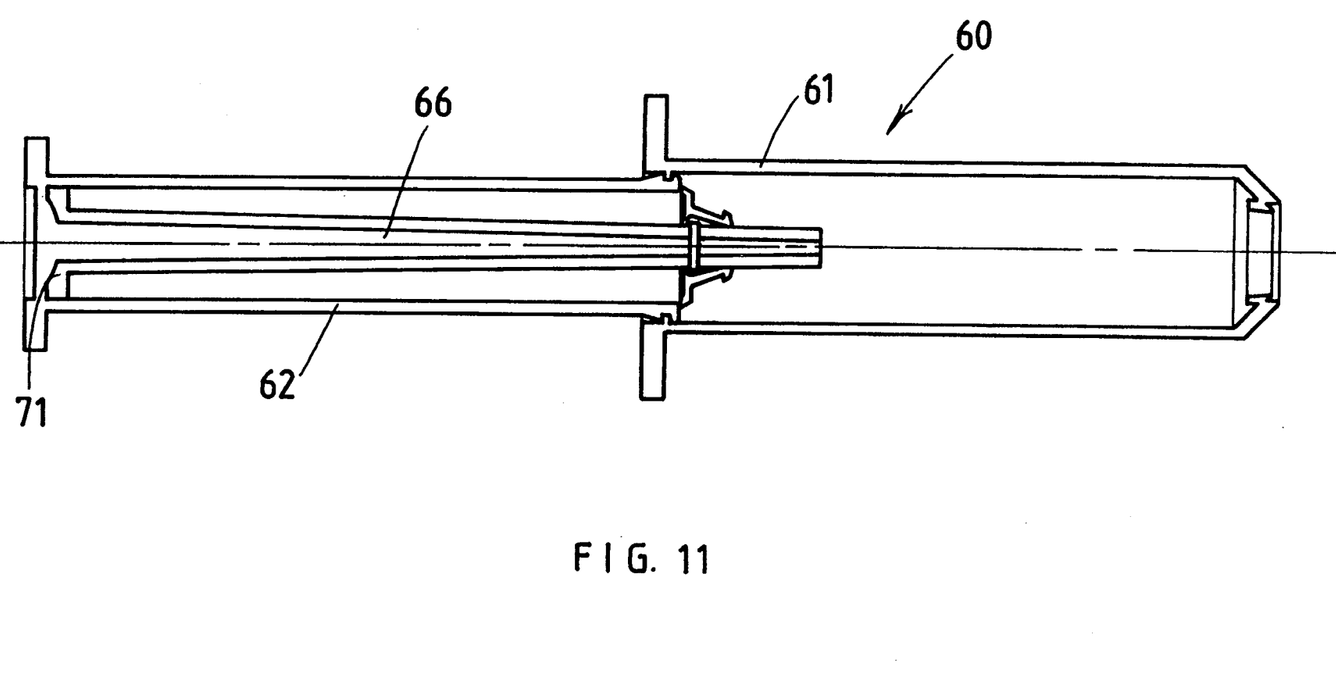

The final action of the barrel end on the clipping formation is shown in FIG. 10 and thereafter withdrawal of the barrel from the sheath takes place (FIG. 11) with the piston being drawn up together with the barrel, thus bringing the needle within the sheath to its safety position.

Figure 13:
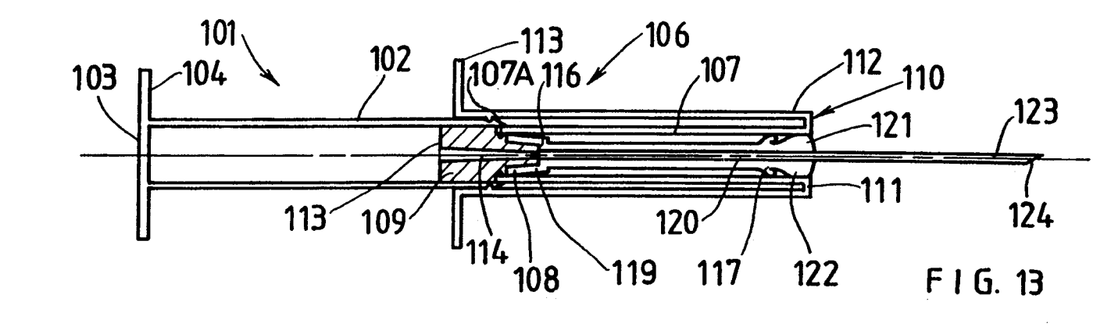
FIG. 13 to 15 are cross sectional side views of a syringe according to a third embodiment of the invention in various stages of operation; and, FIGS. 16 to 18 are cross sectional side view/s of a fourth embodiment of the invention illustrating various stages of operation.

Referring to FIG. 13, a syringe indicated generally by numeral (101) comprises a syringe barrel (102) having an external handle end (103) with a radially extending thumb support (104), and an opposite interior needle end (105). The needle end (105) is located within a protective sheath indicated generally by numeral (106).

The sheath is a double walled tube which has an interior tube (107) with an interior needle end (108) which is attached around an elastomeric or rubber material piston (109). The piston is reciprocable within the barrel 102, in which it is fitted. The interior tube (107) extends from the piston away from the handle end of the barrel (102), in operative orientation, for substantially the length of the travel of the barrel over the piston, to end in an exterior needle end (110).

The exterior needle end (110) is integral with a radially extending skirt (111) which is joined to the exterior sheath tube (112), which is spaced apart around the interior tube (107). The exterior tube (112) extends from the skirt (111) past the needle end (108) of the interior tube, and has radial outwardly extending finger supports (113) therearound, approximately around the position of the piston (109). The spacing between the exterior tube (112) and the interior tube (107) is such that the syringe barrel (102) can slide between the tubes until an inner end (109A) of the piston (109) contacts the interior of the handle end (103) of the barrel.

The piston (109) has an axial opening (114) therethrough which extends from the inner end (109A) to an outer end (116), which is shaped to receive a hypodermic needle means (117).

The hypodermic needle means (117) has at its operative interior end a cap (119) for fitting around the exterior end of the piston, and extends in the form of a support tube, around a steel needle (120) to an exterior end (121). The exterior end (121) is thickened and has formations (122) which ride against the interior surface of the sheath tube (107). These formations can also be slid within the tube (107) if the piston is freed from its attachment to the sheath and moved with the barrel. The needle extends outwardly from the thickened end (121) for a length (123) which ends in a needle point (124).

The piston (109) is attached to the interior tube (107) by means of a bayonet fitting (107A), so that it can be inserted within the end of the sheath, and twisted to lock against axial movement from that position. If the piston is rotated or twisted to the unlocking position it can be axially withdrawn from the sheath tube.

Figure 14:
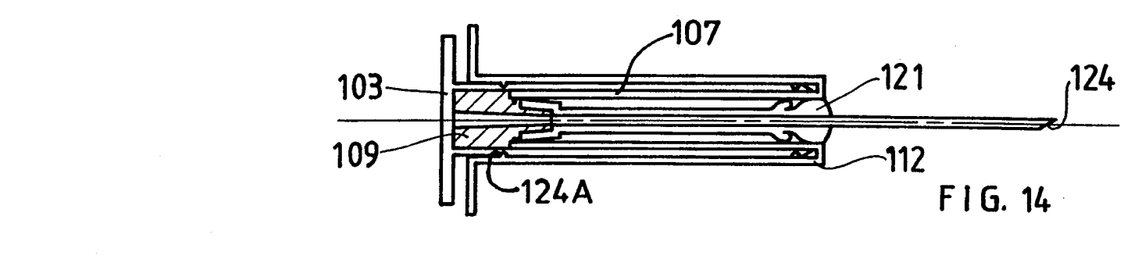

Referring to FIG. 14, the barrel is fully depressed over the piston so that the syringe barrel extends within the tubular space between the interior tube (107) and the spaced apart exterior tube (112) of the sheath.

In use, the syringe in the position described with reference to FIG. 14 is used by inserting the needle into a substance to be injected, and withdrawing the syringe barrel outwardly to the position indicated in FIG. 13. This causes the substance to be drawn up into the syringe barrel through the needle and opening in the piston, to charge the syringe.

The needle is inserted at an injection site, and the injection is given. In this position, the syringe returns to the position described with reference to FIG. 14, with the syringe barrel fully pressed into the sheath and the needle protruding from the end of the sheath.

In order to render the syringe safe, the syringe barrel is now twisted relative to the sheath. The finger supports (113) and (104) are used to achieve this. The twisting action occurs from lock to lock of the bayonet fitting, so that the piston is detached from the end of the sheath.

The friction between the piston and the syringe barrel is sufficient to cause the piston, together with the attached hypodermic needle means, to move with the barrel when the barrel is withdrawn from the sheath. The barrel is now withdrawn, carrying the piston at the handle end with it. This causes the needle to withdraw into the sheath, to be shielded by the housing against accidental contact.

Preferably a one way clip mechanism is provided (124A) so that if the syringe is retracted past a certain position relative to the sheath, it is locked and can no longer be pushed forward in a discharge action. This ensures that the shield will remain around the needle, and will inhibit re-use of the syringe.

Figure 15:
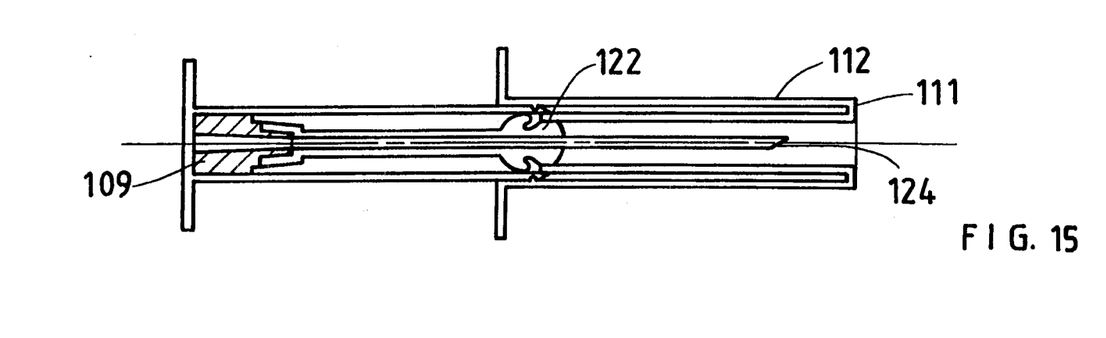
Figure 16:
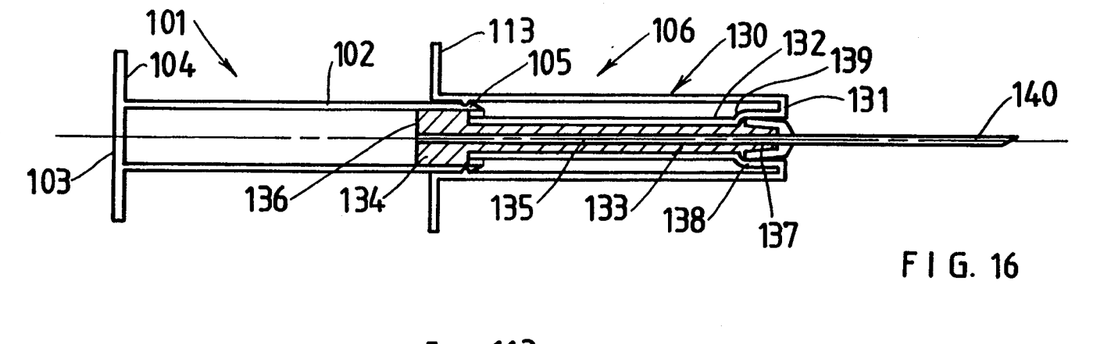
Figure 17:
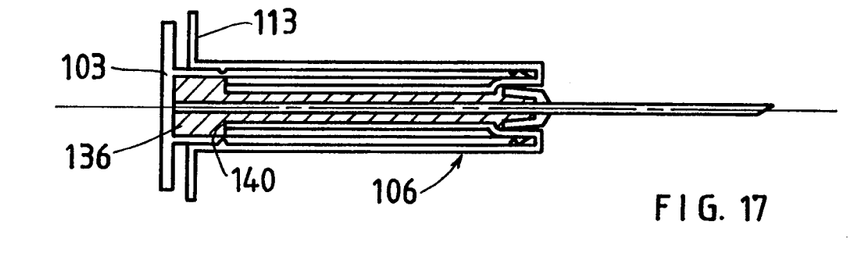
Figure 18:
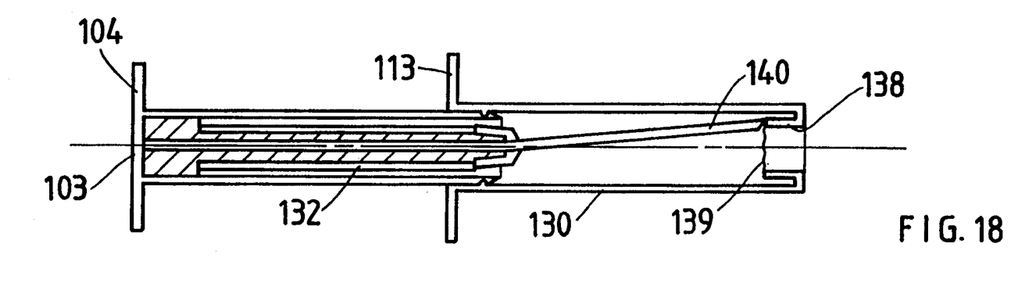

Referring now to FIGS. 16, 17 and 18, a fourth alternative embodiment of the invention is shown. Like numerals in these figures refer to like items as described with reference to FIGS. 13 to 15. In this case however, the interior tube of the sheath (106) is located around an elongate tube section (133) of the piston (134). The piston (134) and its tube section (133) have a central axial opening (135) extending from the interior piston end (136) to an exterior piston end (137) just within the end of the concentric sheath tubes (130) and (132). Surrounding the exterior end (137) of the piston, is an initial section (138) of the interior tube (132) of slightly larger diameter than the remainder of the tube. The radially stepped junction forms an annular line of weakening (139). The exterior piston end (137) is shaped to take a standard hypodermic needle (140).

In use, (FIG. 17), the syringe barrel is depressed with the barrel sliding in between the two concentric tubes (130) and (132) until the interior piston end (136) abuts the interior of the free end (103) of the barrel. The injection liquid is drawn into the barrel by sliding the barrel outwardly to its position described with reference to FIG. 13.

The injection is then given and the barrel returns to its position as described with reference to FIG. 14, where it is fully depressed within the sheath (106).

In this position the piston abuts the interior of the free barrel end (103), and the finger supports (104) of the barrel are spaced apart from the finger supports (113) of the sheath. The piston is secured relative to the inner tube (132) by reason of the tube (132) being located around a narrowed section formed by the extending portion (133) of the piston.

To render the syringe safe, the syringe is held with the handle end of the barrel facing downwardly, and it is knocked sharply against a hard surface. This causes the syringe barrel to move within the housing to the extent of the spacing between the finger supports (104) and (113), thus breaking the interior tube (132) along the lines of weakening (139).

The piston is detached from the sheath and can be withdrawn together with the syringe barrel. As this is done, the needle, which is attached to the exterior end of the piston, is withdrawn into the external tube (130) of the sheath.

A feature of this embodiment provides for a resilient bias in the piston tube to tilt the piston axially to one side, when the barrel reaches the end of its withdrawal travel. This is arranged to cause the end of this piston together with the needle (140) to tilt off centre with the needle point located behind the skirt (138). In this position, if the barrel is depressed again in a discharge motion, the needle will travel forward and be lodged within the space between the skirt (138) and the exterior tube (130).

What we claim as new and desire to secure by Letters Patent is:

1. A syringe comprising: a barrel having a needle end and a handle end; a piston having an operatively inner and an outer end, and which is reciprocable in the barrel with the outer end facing the needle end of the barrel there being a liquid passage between the piston ends, which passage is connectable at the outer piston end to needle means; an open ended generally tubular sheath having a needle end and a handle end, and being slidable over the barrel; connecting means for enabling the sheath and the piston to be attached together with the sheath extending around the barrel, and enabling the sheath and the piston to be selectively detachable from each other with the syringe assembled for use; the sheath being of sufficient axial length to extend to surround needle means attached to the piston in use, when the piston and sheath are detached from each other and the inner piston end is toward the handle end of the barrel and the barrel is retracted from the sheath.

2. A syringe as claimed in claim 1 in which the handle end of the sheath extends over the barrel from the barrel needle end toward the piston inner end when the piston is attached to the sheath in use, and the handle end of the sheath carries finger supports.

3. A syringe as claimed in claim 2 in which the piston is elongate, having a piston head at its inner end which is sealingly reciprocable with the barrel and which has the connection means at its outer end for enabling the piston to be attachable to the sheath.

4. A syringe as claimed in claim 3 in which the connection means includes clip means with release means, operable from the interior of the sheath to unclip the piston assembly from the sheath.

5. A syringe as claimed in claim 4 in which the barrel has a needle end shaped to operate the release means in use, when the barrel is pushed fully into the sheath.

6. A syringe as claimed in claim 5 in which the clip means are radially outwardly biased clips which are clippable over generally radially inwardly directed surfaces of the periphery of the needle end of the sheath.

7. A syringe as claimed in claim 6 in which the clips have surfaces which slope radially outwardly towards the inner piston end in use, to grip the sheath surfaces in barbed manner and restrain axial retraction in a direction away from the needle end, the clip means having tensioning members positioned to bear in use against an inside surface of the sheath end, to draw the engaged clips tightly against the sheath end.

8. A syringe as claimed in claim 6 in which the release means has at least one lever which is generally axially movable to pivot the clips radially inwardly out of engagement with the sheath end.

9. A syringe as claimed in claim 7 in which the release means has at least one lever which is generally axially movable to pivot the c lips radially inwardly out of engagement with the sheath end.

10. A syringe as claimed in claim 9 in which the needle end of the barrel is shaped to be engageable with the release means by abutting a lever of the release means with axial movement of the barrel, to move the lever axially towards the needle end to pivot the clips out of engagement.

11. A syringe as claimed in claim 10 in which the needle end of the barrel is locatable around the ends of the levers when the levers are in a radially inwardly and resiliently compressed position, on first insertion of the barrel into the sheath, the levers being biased to move radially outwardly into the path of axial movement of the barrel, after withdrawal of the barrel end from its location around the lever ends.

12. A syringe as claimed in claim 11 in which the piston is a piston assembly which has a piston head sealingly reciprocable within the barrel, and which has an elongate tapering tubular wedge extending co-axially from the piston head towards the operative needle end of the syringe, and which wedge is located within an outer tubular sheath carrying the clipping means, with the wedge having an axial slot running the full length thereof which, together with the outer sheath, provides the liquid opening through the piston itself.

13. A syringe as claimed in claim 11 in which the piston is a piston assembly which has a piston sealingly reciprocable within the barrel and which has a tube with a tapering tube opening extending from a widest part at the piston head, and carrying the clipping means towards the other end thereof, the barrel carrying a drive rod slidable within, and which tapers to conform with, the interior taper of the tube, so that with the piston head up against the interior of the handle end of the barrel, the drive rod is snugly fitted within the interior of the tapered portion of the tube of the piston assembly.

14. A syringe as claimed in claim 2 in which the sheath is a double walled tube with an interior tube and an exterior tube joined at the needle end, and the piston is attachable to the needle end of the interior tube, which interior tube is reciprocably movable with the piston within the barrel, the barrel being received between the interior and exterior sheath tube during such movement.

15. A syringe as claimed in claim 14 which has an annular line of weakening at the attachment of the interior tube to the piston which is breakable for detaching the piston from the exterior tube of the sheath.

16. A syringe as claimed in claim 15 in which the line of weakening is located on the interior tube at a position removed from the needle end of the sheath, and selected so that an inwardly extending tubular skirt remains after the said breaking along the lines of weakening in use.

17. A syringe as claimed in claim 14 in which formations which hold the sheath in position when the piston is retracted with the barrel, and preferably the formations hold the sheath so that reversal of the action is at least inhibited.

18. A syringe as claimed in claim 17 in which the piston is resiliently biased to cause the piston assembly to tilt off center when the piston is retracted together with the barrel in use, the tilt being arranged to direct an operatively attached needle means towards the sheath wall behind the said remaining skirt.

19. A syringe as claimed in claim 17 in which piston is attachable to, and detachable from, the sheath by means of a rotatable lock.

20. A syringe as claimed in claim 1 in which the piston is shaped to fit within the barrel sufficiently tightly to cause the piston to move with the barrel in use when the piston is detached from the sheath.

21. A syringe as claimed in claim 20 in which the piston is shaped so that it extends in operative location substantially to the free end of the sheath.

* * * * *